United States Patent
Knapp et al.

(10) Patent No.: US 9,990,743 B2
(45) Date of Patent: Jun. 5, 2018

(54) SUPPRESSION OF VASCULAR STRUCTURES IN IMAGES

(71) Applicant: Riverain Technologies LLC, Miamisburg, OH (US)

(72) Inventors: Jason F. Knapp, Miamisburg, OH (US); Praveen Kakumanu, Mason, OH (US); Steve W. Worrell, Miamisburg, OH (US)

(73) Assignee: Riverain Technologies LLC, Miamisburg, OH (US)

( * ) Notice: Subject to any disclaimer, the term of this patent is extended or adjusted under 35 U.S.C. 154(b) by 0 days. days.

(21) Appl. No.: 14/665,652

(22) Filed: Mar. 23, 2015

(65) Prior Publication Data
US 2015/0279034 A1 Oct. 1, 2015

Related U.S. Application Data

(60) Provisional application No. 61/971,042, filed on Mar. 27, 2014.

(51) Int. Cl.
*G06K 9/00* (2006.01)
*G06T 11/00* (2006.01)
(Continued)

(52) U.S. Cl.
CPC .......... *G06T 11/008* (2013.01); *A61B 6/5217* (2013.01); *G06T 5/005* (2013.01);
(Continued)

(58) Field of Classification Search
CPC ......... G06T 11/008; G06T 2207/20016; G06T 2207/20036; G06T 2207/20076; G06T 2207/20148; G06T 7/0012
See application file for complete search history.

(56) References Cited

U.S. PATENT DOCUMENTS

2006/0110020 A1* 5/2006 Foos .................. G06T 7/0012
382/132
2007/0165921 A1* 7/2007 Agam ................ G06T 7/0012
382/128
(Continued)

FOREIGN PATENT DOCUMENTS

EP          2124191 A2    11/2009
WO      2014042678 A1     3/2014

OTHER PUBLICATIONS

International Search Report and Written Opinion dated Jun. 29, 2015 in International Application No. PCT/US2015/022184.
(Continued)

*Primary Examiner* — Gandhi Thirugnanam
(74) *Attorney, Agent, or Firm* — Panitch Schwarze Belisario & Nadel LLP

(57) ABSTRACT

Image processing techniques may include a methodology for normalizing medical image and/or voxel data captured under different acquisition protocols and a methodology for suppressing selected anatomical structures from medical image and/or voxel data, which may result in improved detection and/or improved rendering of other anatomical structures. The technology presented here may be used, e.g., for improved nodule detection within computed tomography (CT) scans. While presented here in the context of nodules within the lungs, these techniques may be applicable in other contexts with little modification, for example, the detection of masses and/or microcalcifications in full field mammography or breast tomosynthesis based on the suppression of glandular structures, parenchymal and vascular structures in the breast.

27 Claims, 7 Drawing Sheets

(51) Int. Cl.
  *A61B 6/00*   (2006.01)
  *G06T 5/00*   (2006.01)
  *G06T 7/00*   (2017.01)
  *G06T 7/136*  (2017.01)
  *A61B 6/03*   (2006.01)

(52) U.S. Cl.
  CPC ............ *G06T 7/0012* (2013.01); *G06T 7/136* (2017.01); *A61B 6/032* (2013.01); *A61B 6/5258* (2013.01); *G06T 2207/10081* (2013.01); *G06T 2207/20016* (2013.01); *G06T 2207/20036* (2013.01); *G06T 2207/20076* (2013.01); *G06T 2207/30064* (2013.01); *G06T 2207/30068* (2013.01); *G06T 2207/30101* (2013.01)

(56) References Cited

U.S. PATENT DOCUMENTS

| | | | |
|---|---|---|---|
| 2007/0211930 A1* | 9/2007 | Dolwick | A61B 6/025 382/132 |
| 2009/0060332 A1* | 3/2009 | Knapp | G06K 9/34 382/173 |
| 2009/0060366 A1* | 3/2009 | Worrell | G06K 9/346 382/256 |
| 2009/0290779 A1* | 11/2009 | Knapp | G06T 5/50 382/132 |
| 2010/0266188 A1* | 10/2010 | Burns | G06T 7/30 382/132 |
| 2010/0266189 A1* | 10/2010 | Knapp | G06T 5/002 382/132 |
| 2010/0322493 A1* | 12/2010 | Wei | G06T 7/0083 382/128 |
| 2012/0269436 A1* | 10/2012 | Mensink | G06K 9/00624 382/180 |
| 2013/0223711 A1* | 8/2013 | Knapp | G06K 9/62 382/131 |
| 2015/0063669 A1* | 3/2015 | Wiemker | G06T 15/08 382/131 |
| 2015/0279034 A1* | 10/2015 | Knapp | G06T 11/008 382/131 |

OTHER PUBLICATIONS

Rohlfing, et al., "Improving Reliability and Performance of Voxel-Based Registration by Coincidence Thresholding and Volume Clipping," Proceedings of Medical Image Understanding and Analysis, Publication [online], 1999. [Retrieved from Internet Jun. 5, 2015]. URL: <http://citseerx.ist.psu.edu/viewdoc/download?doi=10.1.79.8659&rep1&type=pdf>, pp. 1-4.

Li et al., "Computer-aided diagnostic scheme for lung nodule detection in digital chest radiographs by use of a multiple-template matching technique," (2001) Medical Physics, 28(10): 2070-2076.

Armato et al., "Automated detection of lung nodules in CT scans: preliminary results," (2001) Medical Physics, 28: 1552-1561.

Frangi et al., "Multiscale vessel enhancement filtering," (1998) MICCAI 130-137.

Li et al., "Selective enhancement filters for nodules, vessels, and airway walls in two- and three-dimensional CT scans," (2003) Medical Physics, 30(8): 2040-2051.

Wu et al., "Stratified learning of local anatomical context for lung nodules in CT images," (2000) CVPR 2791-2798.

Van Ginneken et al., "Comparing and combining algorithms for computer-aided detectionof pulmonary nodules in computed tomography scans: the ANODE09 study," (2010) Medical Image Analysis, 14(6): 707-722.

Van Rikxoort et al., "Automated segmentation of pulmonary structures in thoracic computed tomography scans: a review," (2013) Physics in Medicine and Biology, 58: 187-220.

Extended European Search Report dated Aug. 17, 2017 in EP Application No. 15767829.3.

Suzuki et al., "How Can a Massive Training Artificial Neural Network (MTANN) Be Trained with a Small Number of Cases in the Distinction Between Nodules and Vessels in Thoracic CT?", Academic Radiology, vol. 12, No. 10, pp. 1333-1341 (2005).

* cited by examiner

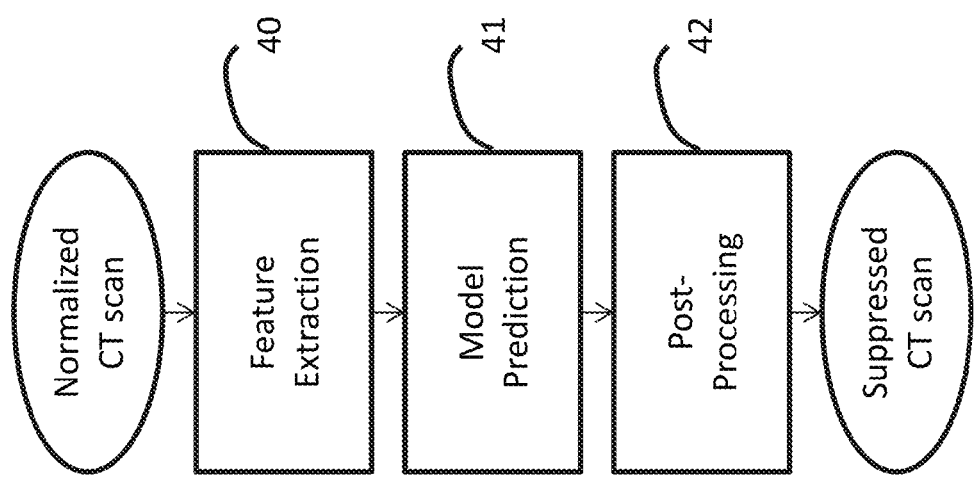

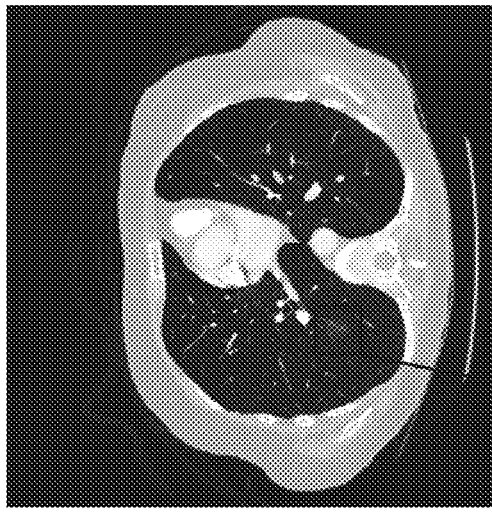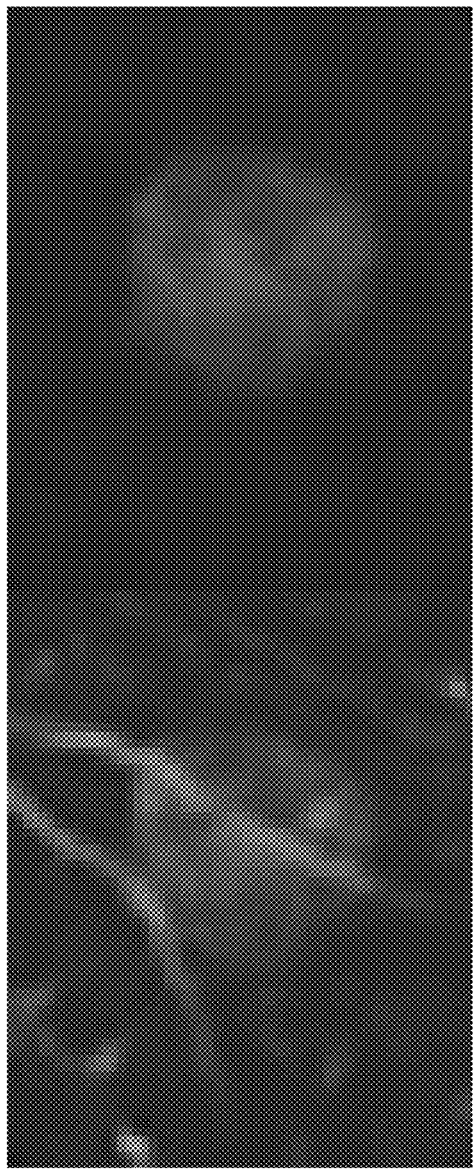

SUPPRESSION OF VASCULAR STRUCTURES IN IMAGES

CROSS-REFERENCE TO RELATED APPLICATION

This application is a non-provisional patent application deriving priority from U.S. Provisional Patent Application No. 61/971,042, filed on Mar. 27, 2014, and incorporated by reference herein.

FIELD OF ENDEAVOR

The present disclosure may relate generally to suppressing unwanted structures within a medical image and/or voxel data using feature extraction and successive model-based prediction methods and may further relate to techniques that may improve detection of lung nodules within computed tomography (CT) scans. Model-based prediction in the context of this disclosure is defined as the use of an analytical model(s), empirical model(s) or combination thereof, e.g., neural network, to predict a value (e.g., a pixel or voxel) based on measures, either computed or derived from pixels/voxels.

BACKGROUND

It is widely recognized that object detection is a challenging problem. There are many aspects that make object detection difficult for computer vision systems, including factors such as variations in image acquisition, complexity of object appearance, and significant variability in object backgrounds (usually referred to as clutter), to name just a few. In the domain of medical imaging, an "object" might refer to a particular component of normal anatomy, the location of a non-anatomical object, or the presence of disease such as a tumor.

One important application of object detection in medical imaging is the detection of lung nodules, or masses, in CT scans of the chest. Despite more than two decades of effort, the general problem of machine nodule detection remains unsolved, and human detection remains limited. We argue that a significant reason for this is a failure to address one significant component of what makes the problem difficult: the complex interaction of nodules with pulmonary vessels, and the variation in appearance due to varying acquisition protocols.

SUMMARY OF THE DISCLOSURE

Various aspects of this disclosure may include an approach for normalizing medical image and/or voxel data captured under different acquisition protocols, and/or a method for suppressing selected non-nodule structures within medical image and/or voxel data of the chest. Most non-nodule structure is vascular content, and therefore, the term "vessel suppression" will be used in this disclosure as a general term for such non-nodule structure suppression. However, the disclosed techniques may also apply to structures other than "vessels"/vascular structures, e.g., bronchial walls and fissure lines in the thorax, as well as, on occasion, man-made objects that take on tubular-like properties. This may further extend to other body parts (e.g., the breast, the heart, the head), other modalities (e.g., ultrasound, tomosynthesis, etc.) and/or other domains (e.g., video surveillance, military targeting). The techniques may be used for the purposes of improved nodule detection, nodule characterization and/or improved rendering of selected anatomically suppressed or enhanced image data. While the techniques are described herein with specific reference to nodules within the lungs, similar methodologies may be applied in other contexts.

Additional features and advantages of various aspects of this disclosure will be apparent from the detailed description that follows, taken in conjunction with the accompanying drawings, which together illustrate, by way of example, features of various aspects of the disclosure.

BRIEF DESCRIPTION OF THE DRAWINGS

In the accompanying drawings:

FIG. 4 shows a process diagram of an example of a prediction phase, according to an aspect of the disclosure;

FIGS. 6A-6C show an image example of a ground glass nodule with vessels removed.

DETAILED DESCRIPTION

Figure 1:
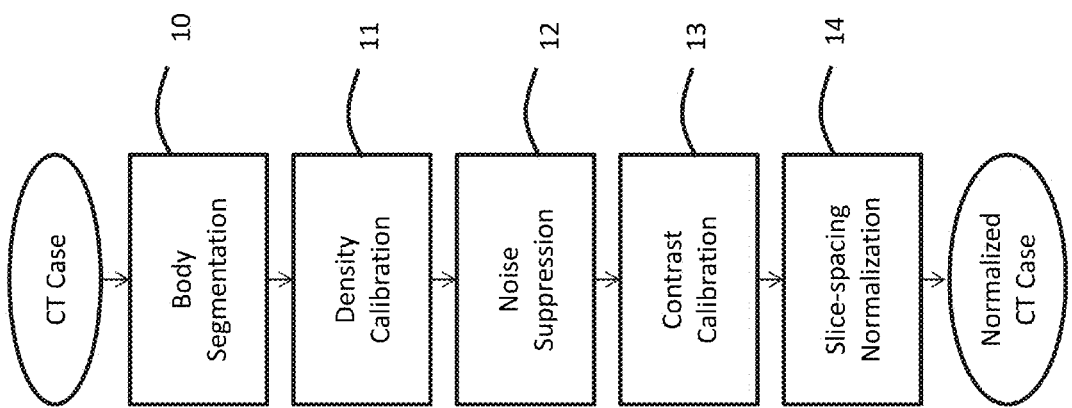
FIG. 1 shows an example of a process diagram, e.g., for CT acquisition normalization, according to an aspect of the disclosure.

There are several approaches that may be taken to nodule detection, which may include template matching (e.g., Q. Li, S. Katsuragawa, and K. Doi, "Computer-aided diagnostic scheme for lung nodule detection in digital chest radiographs by use of a multiple-template matching technique," *Medical Physics,* 2001, 28(10): 2070-2076; hereinafter "Li et al. 2001"), multi-level thresholding (e.g., S. Armato, M. Giger, and H. MacMahon, "Automated detection of lung nodules in CT scans: preliminary results," *Medical Physics,* 2001, 28, 1552-1561; hereinafter "Armato et al. 2001"), enhancement filters (e.g., A. Frangi, W. Niessen, K. Vincken, and M. Viergever, "Multiscale vessel enhancement filtering, "*MICCAI,* 1998, 130-137; hereinafter "Frangi et al. 1998;" and Q. Li, S. Sone. and K. Doi, "Selective enhancement filters for nodules, vessels, and airway walls in two- and three-dimensional CT scans," *Medical Physics* 2003, 30(8): 2040-2051; hereinafter "Li et al. 2003"), and voxel classification (e.g., D. Wu, L. Lu, J. Bi, Y. Shinagawa, K. Boyer, A. Krishnan, and M. Salganicoff, "Stratified learning of local anatomical context for lung nodules in CT images," *CVPR,* 2000, 2791-2798. hereinafter "Wu et al. 2000").

Template matching (e.g., as in Li et al. 2001) may involve measuring the similarity about each voxel to a set of templates. The more varied the object appearance, the more templates may be needed for reasonable performance. This scaling behavior may make template matching inefficient in difficult domains.

Multi-level thresholding may be used in CT (e.g., as in Armato et al. 2001), in part because voxel values, which may be defined in Hounsfield units (HU), may have a meaningful interpretation. Knowledge of nodule density, for example, may be used for setting the thresholds. This technique may encounter some difficulties, one of which may be proper measurement of object morphology for a given threshold. Nodules may be connected to surrounding structures, which may make accurate morphological assessment difficult. To compensate, such approaches may embed a morphological post-processing step to remove connected structures. The morphological post-processing may, however, alter the nodule to such an extent that it may become undetectable. One might adapt this process by using more elaborate post-processing, e.g., rule-driven adaptation, but such rule driven adaption may lead to brittleness, and the method may begin to look more like template matching.

Filter enhancement methods (e.g., as in Frangi et al. 1998 and Li et al. 2003) may improve upon template matching by being adaptive to local structures. One such approach may be to estimate local structure derived from local tensor information. Two example tensors are the 3×3 Hessian matrix and the 3×3 structure tensor, where the "3" refers to the number of spatial dimensions. The eigenvalues from these tensors may be used to quantify the degree of "tubeness", "blobness" or "plateness" at each voxel. These indicators may be combined to derive a composite feature index. While such analysis may be simple and analytically neat, it may encounter some limitations. First, the expressions used to combine the information may be based on idealizations of nodules and vessels that may not be true in reality. For example, nodules are not generally perfect spheres, and vessels are not generally perfect cylinders. As the methods may only use information captured by first- and second-order derivatives, the performance may falter in more complex regions such as where vessels bifurcate or where nodules become attached to vascular structure. Lastly, as the methods are based on idealizations, combining indicators across multiple scales may not be easy.

Voxel classification, e.g., as in Wu et al. 2000, may involve extracting features from a CT scan that may then be used by a classification method to produce probabilities, or other outputs, that may indicate if a nodule is present or not. Voxel classification may need large amounts of manually labeled data, which may be impractical. The voxel classification method may also suffer from sample bias, which means that it may be specifically tuned to the types of nodules collected to train it, which may result in missed nodules.

Another method is found in R. Wiemker, T. Buelow and T Klinder, "Visual Suppression of Selective Tissue in Image Data," U.S. Patent Application Publication No. 2015/0063669 (hereinafter "Wiemker et al. 2015"). In Wiemker et al., the inventors describe a method for suppressing vascular structure as a weighted combination of original data with suppressed data. This type of methodology may often be referred to as "inpainting" in the literature. One such approach to object removal may be pyramid blending. The weight used for blending may be derived from a local likelihood of "vesselness," which may correspond to a value between zero and one. How the measure is actually derived is never described in Wiemker et al. 2015; only its use as a means to blend image data with and without suppression is described. Wiemker et al. describes various modes of modification of the likelihood for emphasizing or deemphasizing the weight. The mechanism for getting the "opacity mappings" of Wiemker et al. is less clear. The description seems to imply that the density of voxels is decreased by a type of look-up table.

It has also been recognized that it may be useful to develop automated methods for nodule detection and segmentation, but which may also provide adjunctive information that may be in the form, e.g., of secondary volumes that can be used by human experts (see, e.g., B. Van Ginneken, S. Armato, et al., "Comparing and combining algorithms for computer-aided detection of pulmonary nodules in computed tomography scans: The ANODE09 study," *Med. Image Analysis,* 2010, 14(6), 707-722, and E. M. Van Rikxoort, B. Van Ginneken, "Automated segmentation of pulmonary structures in thoracic computed tomography scans: a review," *Physics in Medicine and Biology,* 2013, 58, 187-220).

Various aspects of the present disclosure may be related to frameworks built by the present inventors for normal anatomy suppression (see, e.g., U.S. Patent Application Publication No. 2009/0290779 to Knapp et al. (hereinafter, "Knapp et al. 2009") and U.S. Patent Application Publication No. 2013/0223711 to Knapp et al. (hereinafter, "Knapp et al. 2013"), both of which are incorporated by reference herein). In Knapp et al. 2009), models were built by predicting an alternative image where the density of bones is removed. In Knapp et al. 2013, a pectoral muscle suppression technique may predict image data where the bias associated with the pectoral muscle is removed.

In the context of the present disclosure, use of the term "suppression" implies that anatomical structures (such as vessels) are actually removed from an image and are not simply made less dense. Aspects of the present disclosure may relate to building a prediction model that may "predict out" undesired density, as will be described further below.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

In identifying nodules in a CT scan, one may ideally like to take the CT scan and to suppress structures other than nodules. To start this process each scan may be normalized to account for variations associated with acquisition. This may enhance robustness and simplify further processes. The main steps in this normalization process, according to an aspect of this disclosure, may be seen in FIG. 1. The normalization process may begin with "body segmentation" 10, in which a patient's body may be segmented from other structures within the field-of-view of the input CT image, and may subsequently segment the air regions associated with the patient's respiratory system. Following this, the air region may be calibrated 11 to a fixed value so that the lung density remains near a fixed value. After density calibration 11, the CT scan's noise properties may be analyzed, and an adaptive local averaging method may be used in order to suppress noise artifacts 12. Following noise suppression 12, the image may be processed so that the contrast detail is as consistent as possible from one scan to the next 13. This may be achieved, e.g., using techniques similar to those used in Knapp et al. 2009 and U.S. Patent Application Publication No. 2010/0266189 to Knapp et al. (hereinafter, "Knapp et al. 2010;" Knapp et al. 2010 is also incorporated by reference herein), in which histogram matching was used on a multi-scale representation in order to calibrate contrast detail. Lastly, the volume may be resized (resampled to a specified size, e.g., in millimeters), which may be performed in-plane (within a CT image) and/or out of plane (across CT images), which may involve using interpolation, so that slice spacing and thickness may be made as consistent as possible from one scan to the next 14; this may, again, use techniques described in Knapp et al. 2009 and/or Knapp et al. 2010.

In order to perform vessel suppression, given a volume, one may wish to generate a volume with the vessels predicted out, while being careful not to remove other structures such as nodules. This may be achieved by a strategy of "forward through simulation, inversion with prediction," which will be clarified in the subsequent discussion.

Figure 2:
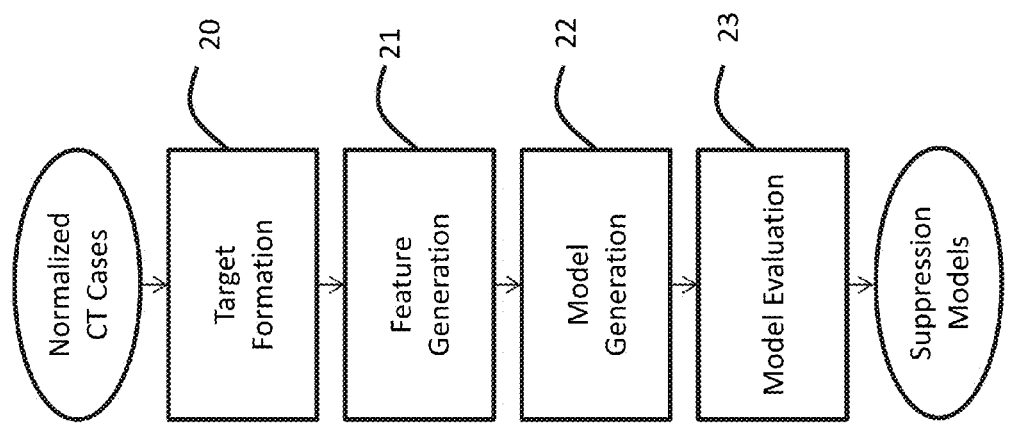
FIG. 2 shows a further process diagram, showing further processing according to various aspects of the disclosure.
Figures 3A, 3B, 3C:
FIGS. 3A and 3B show an example of a slice of a volume before and after nodule simulation.
FIG. 3C shows the same slice shown in FIG. 3B after vessel suppression.

FIG. 2 shows an example of an overall process flow according to an aspect of this disclosure. The process may begin with case selection, i.e., a set number of CT volumes of the thorax that capture a representative amount of normal (anticipated) variability. Using these selected cases, which may have been normalized for acquisition variation, a vessel suppressed volume may be generated for the purpose of model construction, shown in FIG. 2 as target formation 20. In one technique that may be used to create a vessel-suppressed volume (to which the invention is not limited), one may first compute a local minimum intensity projection (min-ip) along the axial direction of the CT volume. This min-ip operation may serve to suppress all, or substantially all, content within the lung fields. The min-ip volume may be blended with the CT volume using a slightly smoothed version of the segmented vessel mask, or in order to suppress all structures, may blended with the CT volume with a mask of known nodule locations. The vessel and/or nodule masks may be generated using an automated algorithm or a semi-automated method; or they may be derived from manual outlines. As these masks are to be used solely for the offline process of creating target data, the actual mechanism used to create them is not essential; however, the more accurate they are, the better. In order to have a sufficient number of examples of nodules interacting with pulmonary vessels, one may use nodule simulation, e.g., as in Knapp et al. 2009. That is, synthetic nodules may be inserted into the unsuppressed and/or vessel-suppressed volumes. The result may be a pair of volumes with and without vessels, but both with unaltered, or substantially unaltered, nodules. FIG. 3A is a slice from a represented example, while in FIG. 3B we see the same slice, only with simulated nodules added. In FIG. 3C we see the same slice from FIG. 3B, only with vessels suppressed, and in which the nodules have been left unaltered.

Once the pairs of input-target volumes are created 20, one may process each image by passing it through a feature generation process 21. This process may be used to extract voxel-level features, where an example set of features may be as follows:

Multi-scale Gaussian derivatives with a range of orders;
Local minimum and maximum intensity projections;
In-plane features computed from and/or on the local minimum and maximum intensity projections.

Other features may be derived based on location or the derivative features themselves (shape indices, curvature, etc . . . ) or learned using model-based approaches, such as patch analysis or deep neural networks. Given the large collection of data, a model, or a set of models, may be generated 22. According to one aspect of this disclosure, multi-layer feed-forward neural networks may be used for this purpose. These models may subsequently be able to predict suppressed data, without the use of a segmentation mask or object indicators, similar to methods found in Knapp et al. 2013. Once a model or set of models have been built, their performance on validation data can be assessed 23. This may lead to the selection of a particular subset of models and/or could be used to further guide the training process by the selection of additional cases for training or the creation of more simulated nodules.

FIG. 4 depicts an example of a high-level flow diagram from a normalized CT scan to a suppressed scan, according to aspects of this disclosure. The extracted features 40 may be the same as those used in model generation 22. The prediction phase 41 may involve applying a set of prediction models, e.g., neural networks, whose outputs may be combined. The combining may be performed, e.g., by averaging, by using a cost function to select an optimal one of the outputs, or both (i.e., selecting an optimal set of outputs to average). In this aspect of the disclosure, multiple model outputs may be obtained for multiple image zones, where each image zone may be identified by its anatomical location and/or by its pixel density. Post-processing 42 may be used to adjust for the normalization process so that the suppressed volume is in-line with the original image data, if desired for display purposes, as it may not be needed for computer-aided detection.

Figure 5:
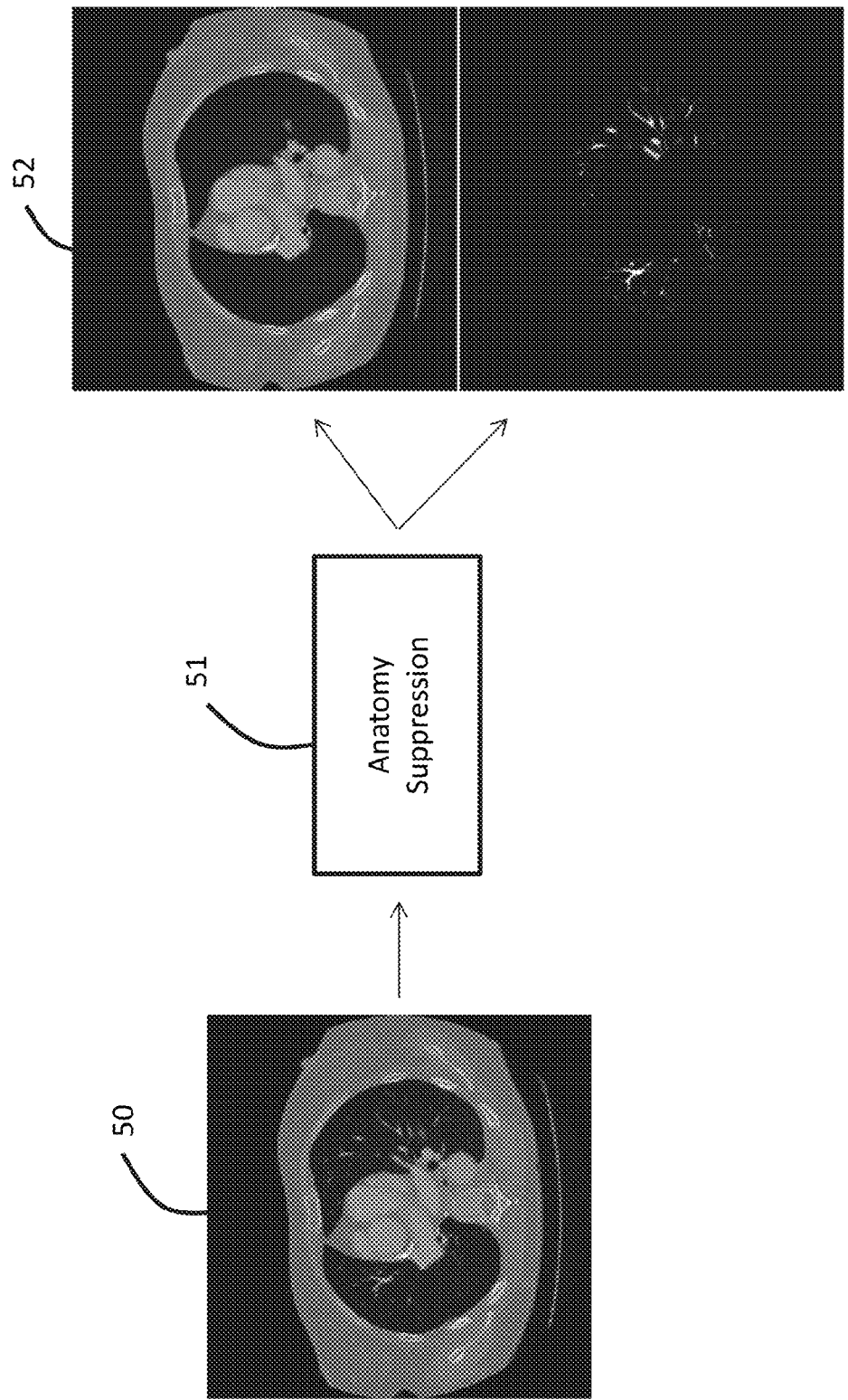
FIG. 5 provides a conceptual depiction of tissue separation, according to an aspect of the disclosure.

FIG. 5 provides a conceptual example of how the overall technique may operate on a real nodule and may generate two representations. An image 50 may undergo anatomy suppression 51, to result in two representations 52. The upper representation in 52 may be a suppressed volume, which may allow for easier detection and segmentation of nodules; and the lower representation in 52 may be a vessel volume, which may simply be the difference between the CT data and the suppressed data. The vessel volume may be useful, e.g., for vessel segmentation or registration with prior scans.

FIG. 6, consisting of FIGS. 6A-6C is an up-close view of an example of a real ground glass nodule with apparent vessel superposition. FIG. 6A shows the CT image. FIG. 6B shows an up-close view of the ground glass nodule image, and FIG. 6C shows a vessel-suppressed image. As can be seen, the algorithm may remove the vascular structure while preserving the nodule content.

Figure 7:
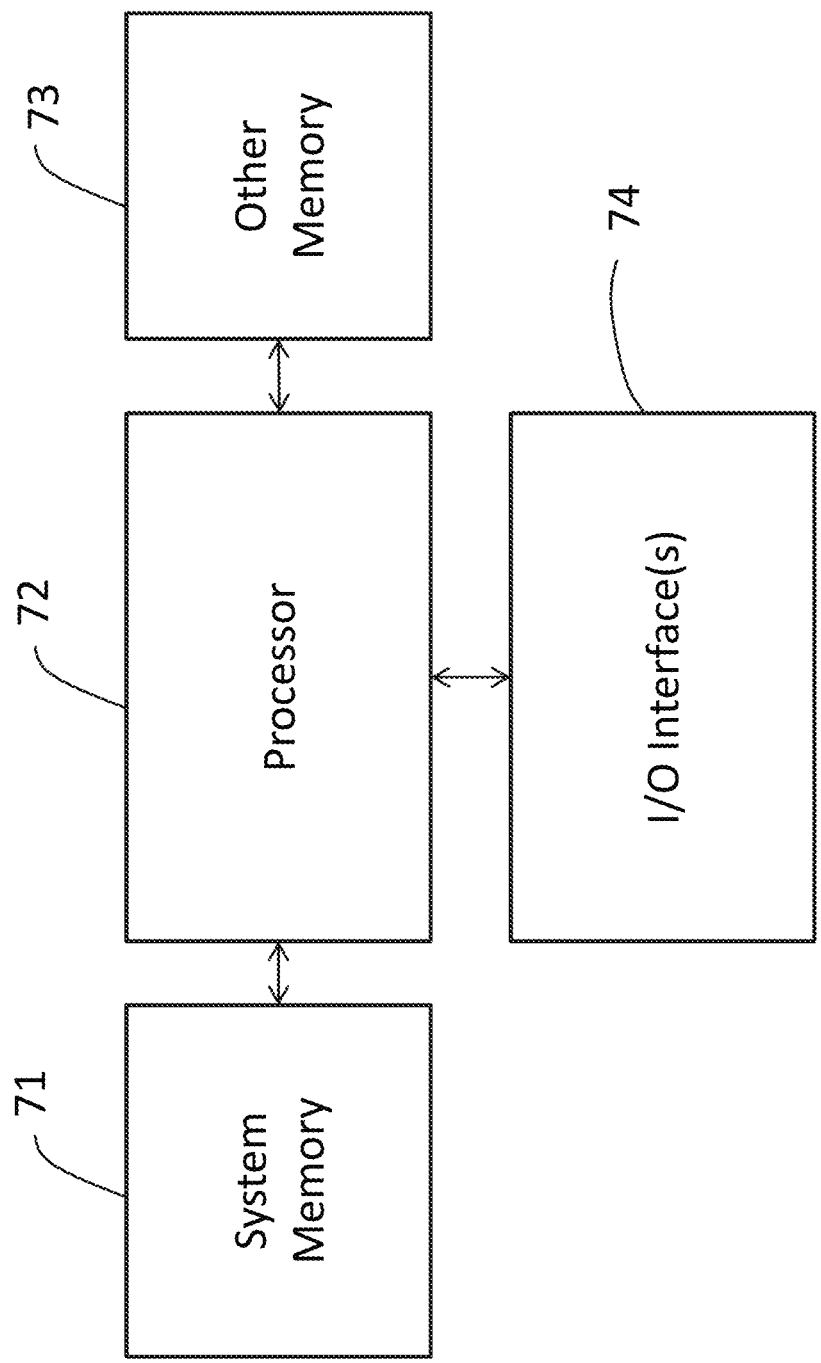
FIG. 7 shows a conceptual diagram of a system in which various aspects of the disclosure may be implemented.

Various embodiments of the invention may comprise hardware, software, and/or firmware. FIG. 7 shows an exemplary system that may be used to implement various forms and/or portions of embodiments according to various aspects of this disclosure. Such a computing system may include one or more processors 72, which may be coupled to one or more system memories 71. Such system memory 71 may include, for example, RAM, ROM, or other such machine-readable media, and system memory 71 may be used to incorporate, for example, a basic I/O system (BIOS), operating system, instructions for execution by processor 72, etc. The system may also include further memory 73, such as additional RAM, ROM, hard disk drives, or other processor-readable media. Processor 72 may also be coupled to at least one input/output (I/O) interface 74. I/O interface 74 may include one or more user interfaces, as well as readers for various types of storage media and/or connections to one or more communication networks (e.g., communication interfaces and/or modems), from which, for example, software code may be obtained or provided (e.g., by downloading or uploading).

It is to be understood that the above-referenced arrangements are only illustrative of the application for the principles of the present invention. Numerous modifications and alternative arrangements can be devised as described in the usage and extension to other applications and domains sections without departing from the spirit and scope of the present invention.

To elaborate, generation of a vessel-suppressed volume may have many uses outside nodule detection and characterization. These may include:

Simpler and more robust segmentation of vessels, which can be used as inputs to other processes, such as pulmonary embolism detection;

Improved vessel tree navigation to biopsy nodules attached to the vessels based on improved visualization of the vascular tree;

Improved detection of disease related to the vascular structure that leads the thickening and/or constriction of the vessels;

Use of the vessel volume, or segmented mask, as an input to a scan registration process, thus allowing for assessment of any potential abnormal changes, such as nodule growth;

Use of the suppressed volume to generate a more-informative display, such as the generation of a maximum intensity projection of the lung (which may, in effect, provide a high-level indication of where nodules may be located);

Two-dimensional reconstructions with both bones and vessels suppressed.

Furthermore, the present techniques may be applied in other applications/domains. Many extensions of the framework presented above go beyond vessel suppression, and the following is merely a list (which is not intended to be exhaustive) of some further applications:

Vessel suppression in the brain for highlighting cerebral aneurysms;

Vessel suppression in CT liver scans for highlighting nodules and improving the ability to segment the vascular structure, perhaps for registration purposes;

Vessel suppression in fundus images of the eye for highlighting micro-aneurysms and other diseases;

Vessel suppression in the breasts (volumes or images acquired via tomosynthesis or mammograms, respectively) for detection or removal of benign calcification, for use in registration or other processes.

While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A method of image processing, including:
a first, offline process, performed prior to processing one or more input images or image volumes, wherein the first, offline process is configured to create paired data based on measured and synthetic data, wherein a first of the paired data consists of created target data, and wherein a second of the paired data consists of an observable result based on output from a measurement device, comprising:
obtaining one or more image components from data representing one or more images or image volumes, the obtaining comprising:
normalizing and pre-processing the data to obtain processed data with target gray scale and sampling characteristics;
extracting features from the processed data to obtain a set of extracted features; and
performing model-based prediction derived from the measured and synthetic data, or derivatives thereof, using at least one neural network regression model, including a deep neural network model, based on the set of extracted features, to predict one or more components based on the target data, wherein the synthetic data, or derivatives thereof, comprises the data representing one or more images or image volumes or data representing the one or more images or image volumes, or both, with the one or more components removed, and data representing one or more simulated structures incorporated into the data representing one or more images or image volumes or data representing the one or more images or image volumes, or both, with the one or more components removed; and
a second process, performed on the one or more input images or image volumes, and performed following the first process, comprising:
removing from data representing the one or more input images or image volumes at least one of the one or more components predicted by the model-based prediction derived through a training process using a combination of the measured and synthetic data, to obtain one or more images and/or image volumes having suppressed components.

2. The method of claim 1, the first process further comprising: obtaining a prediction output with one or more of the components removed.

3. The method of claim 1, wherein the removing comprises:
subtracting one or more components predicted by the deep neural network regression model-based prediction of the first process from the data operated upon by the second process to obtain data with the one or more components removed.

4. The method of claim 1, wherein the data of the second process comprises a radiographic CT series, and wherein the one or more components comprise only vascular components.

5. The method of claim 1, wherein the data of the second process comprises a radiographic CT series, and wherein at least one of the one or more components comprises only nodular structures.

6. The method of claim 1, the first process further comprising inserting simulated nodules into measured original volumes and corresponding anatomy-suppressed volumes, as part of the training process.

7. The method of claim 1, wherein said normalizing and pre-processing includes:
performing noise suppression to obtain noise-suppressed data; and
performing a bandpass decomposition on the noise-suppressed data.

8. The method of claim 7, wherein said normalizing and pre-processing further comprises:
performing at least one operation on at least one result of said bandpass decomposition, wherein the at least one operation is selected from the group consisting of: gray scale registration and enhancement.

9. The method of claim 6, wherein said normalizing and pre-processing includes:
data resizing to obtain target resized data.

10. The method of claim 1, wherein said extracting features includes:
obtaining Gaussian derivatives across different scales.

11. The method of claim 1, wherein said performing model-based prediction derived from the synthetic data and measured data, or derivatives thereof, comprises:

constructing one or more target images or volumes by removing components from one or more corresponding original images or volumes;

inserting one or more target objects, including simulated target objects, measured target objects, or both, in the one or more original images or volumes and the one or more target images and volumes;

applying multiple prediction models to obtain multiple suppressed predictions for one or more volume voxels; and combining the multiple suppressed predictions to obtain a combined estimate.

12. The method of claim 11, wherein said combining the multiple suppressed predictions comprises at least one of averaging the multiple suppressed predictions or selecting an optimal suppressed prediction based on a specified cost function.

13. The method of claim 1, wherein said performing neural network regression model-based prediction comprises:

applying multiple deep neural network regression prediction models corresponding to multiple image zones to obtain predictions for the pixels/voxels of the multiple image zones, wherein the image zones are defined based on anatomical location, on voxel density values, or on both.

14. The method of claim 1, further comprising: downloading software instructions to implement said first process and said second process.

15. A non-transitory machine-readable storage medium containing instructions designed to implement operations comprising:

a first, offline process, performed prior to processing one or more input images or image volumes, wherein the first, offline process is configured to create paired data based on measured and synthetic data, wherein a first of the paired data consists of created target data, and wherein a second of the paired data consists of an observable result based on output from a measurement device, comprising:

obtaining one or more image components from data representing one or more images or image volumes, the obtaining comprising:

normalizing and pre-processing the data to obtain processed data with target gray scale and sampling characteristics;

extracting features from the processed data to obtain a set of extracted features; and performing model-based prediction derived from the measured and synthetic data, or derivatives thereof, using at least one neural network regression model, including a deep neural network model, based on the set of extracted features, to predict one or more components based on the target data, wherein the synthetic data, or derivatives thereof, comprises the data representing one or more images or image volumes or data representing the one or more images or image volumes, or both, with the one or more components removed, data representing one or more simulated structures incorporated into the data representing one or more images or image volumes or data representing the one or more images or image volumes, or both, with the one or more components removed; and a second process, performed on the one or more input images or image volumes, and performed following the first process, comprising:

removing from data representing the one or more input images or image volumes one or more of the components predicted by the model-based prediction derived through a training process using a combination of the measured and synthetic data, to obtain one or more images and/or image volumes having suppressed components.

16. The medium of claim 15, wherein the first process further comprises: obtaining a prediction output with the one or more components removed.

17. The medium of claim 15, wherein the second process further comprises:

subtracting the one or more components from the data operated upon by the second process to obtain data with the one or more components removed.

18. The method of claim 1, wherein the one or more images or image volumes comprise a radiographic image, and wherein the one or more components comprise one or more structures normally found in such a radiographic image.

19. A method of constructing an alternative projection comprising using an anatomical suppressed volume obtained by the method of claim 1.

20. The method of claim 19, further comprising displaying the alternative projection.

21. The method of claim 19, further comprising performing disease detection, segmentation, or registration of the anatomical suppressed volume with a different volume.

22. The method of claim 19, further comprising using the alternative projection to register the data operated upon by the second process with second data from a different modality from a modality used to obtain the data operated upon by the second process.

23. An apparatus comprising:
at least one processor; and
the computer-readable medium according to claim 15.

24. The method of claim 1, further comprising creating one or more images or image volumes displaying the one or more of the components predicted by the model-based prediction.

25. The method of claim 1, wherein the obtaining further includes:

creating one or more models for the model-based prediction, the creating comprising:

adding to data representing one or more further images one or more predetermined simulated image features to create one or more input-target image pairs; and generating the one or more models based on the one or more input-target image pairs.

26. The medium of claim 15, wherein the obtaining further includes:

creating one or more models for the model-based prediction, the creating comprising:

adding to data representing one or more further images one or more predetermined simulated image features to create one or more input-target image pairs; and generating the one or more models based on the one or more input-target image pairs.

27. The medium of claim 15, the first process further comprising inserting simulated nodules into measured original volumes and corresponding anatomy-suppressed volumes, as part of the training process.

* * * * *